(12) United States Patent
Kocurek

(10) Patent No.: US 6,493,889 B2
(45) Date of Patent: Dec. 17, 2002

(54) COOLING COVER APPARATUS

(75) Inventor: Earnest Kocurek, Austin, TX (US)

(73) Assignee: Project Cool Air, Inc., Waco, TX (US)

( * ) Notice: Subject to any disclaimer, the term of this patent is extended or adjusted under 35 U.S.C. 154(b) by 19 days.

(21) Appl. No.: 09/771,915

(22) Filed: Jan. 29, 2001

(65) Prior Publication Data

US 2002/0100121 A1 Aug. 1, 2002

(51) Int. Cl.[7] .................................................. A61F 7/00
(52) U.S. Cl. .............................. 5/423; 5/502; 607/104; 607/107
(58) Field of Search ................................ 607/104, 107, 607/114; 5/421, 423, 726, 502

(56) References Cited

U.S. PATENT DOCUMENTS

| | | | |
|---|---|---|---|
| 4,660,388 A | | 4/1987 | Greene, Jr. |
| 4,884,304 A | | 12/1989 | Elkins |
| 5,265,599 A | * | 11/1993 | Stephenson et al. .......... 165/46 |
| 5,749,109 A | * | 5/1998 | Kappel ........................ 165/96 |
| 5,817,147 A | * | 10/1998 | Wolf ........................... 126/204 |
| 5,989,285 A | | 11/1999 | DeVilbiss et al. |
| 6,171,333 B1 | * | 1/2001 | Nelson et al. ................. 5/485 |

* cited by examiner

*Primary Examiner*—Michael F. Trettel
(74) *Attorney, Agent, or Firm*—Michael B. Jolly

(57) ABSTRACT

A cooling cover apparatus including a top sheet, a bottom sheet secured to the top sheet, a plurality of tubular members positioned between the top sheet and the bottom sheet, a flexible hose interconnected to the plurality of tubular members, and a cooling air generator connected to the flexible hose so as to pass cooling air through the flexible hose and into the plurality of tubular members. A diverter is connected to the flexible hose so as to cause cooling air to selectively enter at least one of the plurality of tubular members. Each of the plurality of tubular members has opening formed therein so as to cause cooling air to pass downwardly through said bottom sheet.

9 Claims, 4 Drawing Sheets

COOLING COVER APPARATUS

BACKGROUND OF THE INVENTION

1. Field of the Invention

The present invention relates to temperature controlled blankets and temperature controlled bedding assemblies. More particularly, the present invention relates to blankets and covers whereby cooling air can be passed by a cooling air generator into the interior of the blanket so as to provide a cooling effect to a person resting below the blanket.

2. Description of Related Art

Several bedding devices have been developed previously for providing heat to a person lying in a bed. Electric blankets containing electric heating elements have been used for many years to warm the occupant of a bed. However, in certain circumstances, the occupant of the bed may desire to have a "cooling" effect rather that the heating effect of an electric blanket. The need for a cooling effect can be quite prominent in areas of the country having relatively high ambient temperatures. If a cooling blanket could be provided, then the air conditioning requirements could be reduced. As a result, the expense associated with air conditioning the bedroom could also be reduced.

Unfortunately, it is very difficult to configure a proper "cooling" blanket in contrast to the relative ease with which an electric blanket can be formed. When a cooling blanket is needed, an external apparatus is required so as to create the "cooling" effect. Such an external apparatus can have a high noise level and can be relatively inexpensive. As such, a need has developed in order to provide a cooling blanket which is energy efficient and economical.

In the past, various patents have issued relating to such cooling blanket apparatus. For example, U.S. Pat. No. 4,660,388, issued on Apr. 28, 1987, to G. J. Greene, Jr., describes a cooling cover having an air inflatable pad which can be positioned within a pocket of a coverlet. The pad is formed of air impermeable material having plenum chambers at opposite ends thereof. A plurality of individual longitudinally extending passages extend between the plenum chambers. Openings or air orifices of a non-uniform pattern in the lower rounded surfaces of the inflatable pad direct cooling air in a plurality of small air jets onto the body of a user of the cooling cover. A source of cool air is connected to the inlet for a plenum chamber to deliver cool air to the pad. U.S. Pat. No. 4,884,304, issued on Dec. 5, 1989 to W. Elkins, describes a bedding system that has a provision for heating or cooling. A sealed three-ply heat transfer and insulating device covers the mattress, below the contour sheet or other covering which comes into contact with the person's body. A wicking contour sheet, capable of absorbing any condensation on the surface of the three-ply device, can also be utilized. A flow of coolant liquid at a regulated temperature close to human skin temperature can be channeled between the lower two plies of the three-ply material. Above these two plies, i.e. between the middle ply and the upper ply, is a sealed envelope containing slightly pressurized air. U.S. Pat. No. 5,989,285, issued on Nov. 23, 1999 to DeVilbiss et al. describes a temperature controllable blanket suitable for heating or cooling a patient. Counterflow or co-flow heat exchanging principles between the temperature controlled liquid and the temperature controlled gas achieves temperature uniformity across different sections of the blanket and the bedding system. Drapes in the temperature controlled bedding system provide a gas envelope around a person using the bedding system. The air portion of the bedding system is provided for use with a patient bed which supplies the fluid portion of the overall bedding system.

The difficulty with these prior art systems is the relatively large expense associated therewith. Each of these systems utilizes relatively complex configurations of components so as to achieve the "cooling" effect. Additionally, and furthermore, certain of these systems use a cooling liquid. Such a cooling liquid can have the potential for leakage. Additionally, complicated "envelope" or supporting structures are required so as to carry out the requisite cooling effect.

It is an object of the present invention to provide a cooling cover apparatus which is simple to use and relatively inexpensive.

It is an another object of the present invention to provide a cooling cover apparatus which requires a minimal number of components.

It is a further object of the present invention to provide a cooling cover apparatus which has a texture and feel closely resembling a conventional cover of a bed.

It is a further object of the present invention to provide a cooling cover apparatus which distributes cooling air toward the upper torso of the person in the bed.

It is a further object of the present invention to provide a cooling cover apparatus which minimizes the noise level within the bedroom.

These and other objects and advantages of the present invention will become apparent from a reading of the attached specification and appended claims.

BRIEF SUMMARY OF THE INVENTION

The present invention is a cooling cover apparatus comprising a top sheet, a bottom sheet secured to the top sheet, a plurality of tubular members positioned between the top and bottom sheets, a flexible hose interconnected to the plurality of tubular members, and a cooling air generator connected the flexible hose so as to pass cooling air through the flexible hose and into the plurality of tubular members. Each of the plurality of tubular members has openings formed therein so as to direct a cooling air flow toward the bottom sheet. A diverter is connected to the flexible hose so as to cause cooling air to selectively enter at least one of the plurality of tubular members.

In the preferred embodiment of the present invention, each of the plurality of tubular members comprises a foam insert having a plurality of holes formed therein, and a non-porous cover affixed to the foam insert. The flexible hose is connected to an end of the foam insert and the non-porous cover. The plurality of holes are formed only in the half of the foam insert opposite the flexible hose. The plurality of tubular members comprises two tubular members in spaced parallel relationship. The top sheet and the bottom sheet are affixed to each other between the two tubular members.

In an alternative embodiment of the present invention, the plurality of tubular members comprises a first set of tubes and a second set of tubes. Each of the tubes of the first set is in spaced parallel relationship to each other. The flexible hose has a first portion connected to a first manifold communicating with the first set of tubes. Each tube of the second set of tubes is arranged in spaced parallel relationship. The flexible hose has a second portion connected to a second manifold communicating with the second set of tubes. Each tube of the first and second sets has a plurality of holes formed therealong. A diverter is connected to the flexible hose and to the first and second portions for selectively passing cooling air to at least one of the first and second sets of tubes.

In another embodiment of the present invention, the plurality of tubular members comprises a first set of cloth tubes formed between the top and bottom sheets and a second set of cloth tubes formed between the top and bottom sheets. Each cloth tube of the first and second sets opens to a respective manifold. The flexible hose has first and second portions respectively connected to the manifolds of the first and second sets of cloth tubes. The cloth tubes are formed by threadedly securing the top sheet to the bottom sheet so as to define the first and second sets of cloth tubes therebetween. A diverter is connected to the flexible hose and to the first and second portions thereof. The diverter serves to selectively pass cooling air into at least one of the first and second sets of cloth tubes.

In still another embodiment of the present invention, the plurality of tubular members comprises a first set of ducts positioned and a second set of ducts positioned between the top and bottom sheets. Each duct of the first set of ducts has an end opening to a first distribution area. The flexible hose has a first portion communicating with the first distribution area. Each duct of the second set of ducts opens to a second distribution area. The flexible hose has a second portion communicating with the second distribution area. Each duct of the first and second sets includes at least one cloth strip extending generally transversely between the top and bottom sheets so as to define the duct as a space between the top and bottom sheet. Each duct of the first and second sets opens at an end opposite the respective distribution areas. A diverter is connected to the flexible hose and to the first and second portions thereof. The diverter selectively passes cooling air into at least one of the first and seconds sets of ducts.

In the preferred embodiment of the present invention, the cooling air generator is a rolling piston compressor. Also, in the preferred embodiment of the present invention, the top sheet and the bottom sheet are secured together so as to define a first overhang area on one side thereof and a second overhang area on an opposite side thereof. The plurality of tubular members are positioned entirely between these overhang areas.

DETAILED DESCRIPTION OF THE INVENTION

Figure 1:
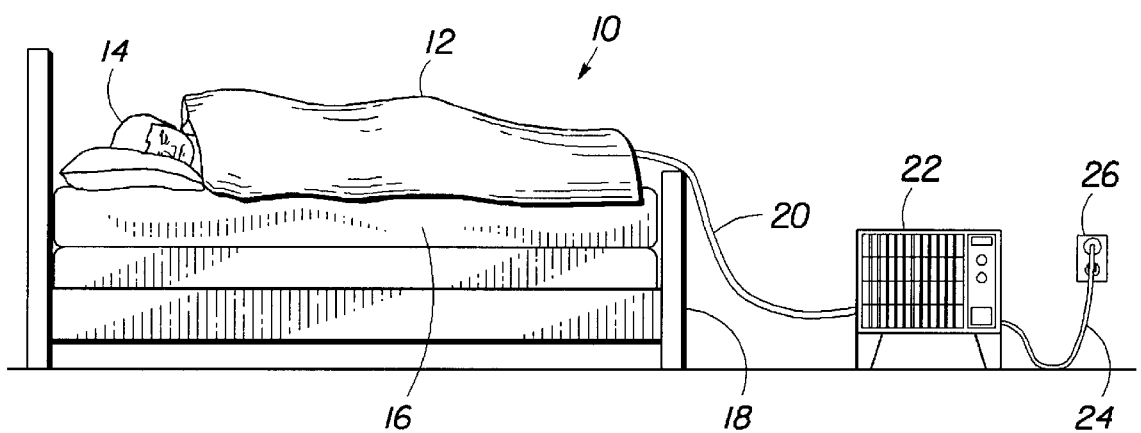
FIG. 1 is a side elevational view showing the application of the cooling cover apparatus of the present invention.
Figure 9:
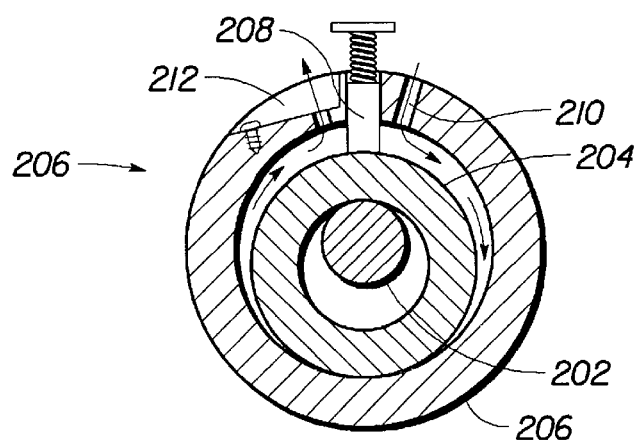
FIG. 9 is a cross-sectional view showing a rolling piston compressor used as the cooling air generator apparatus in the preferred embodiment of the present invention.

Referring to FIG. 1, there is shown at 10 the cooling cover apparatus in accordance with the teachings of the present invention. The cooling cover apparatus 10 includes a cooling cover 12 covering an individual or a person 14 positioned on a mattress 16 of bed 18. The cooling cover 12 includes a plurality of flexible sheets which are joined together along their periphery with a plurality of tubular members extending therebetween. A flexible hose 20 is connected to a cooling air generator 22. Flexible hose 20 is connected to the plurality of tubes between the top and bottom sheets associated with cover 12 so as to provide the cooling air effect to the person 14 on the mattress 16. The cooling air generator 22 is connected by an electrical line 24 for a standard outlet 26. The cooling air generator 22 should be sufficiently quiet so as to produce sound under fifty-five decibels. In the preferred embodiment of the present invention, the cooling air generator 22 will be a rolling piston compressor (as illustrated in greater detail in FIG. 9).

Through the use of the cooling cover apparatus 10 of the present invention, the person 14 is suitably cooled while resting on the mattress 16. The cooling air generator 22 will provide sufficient cooling air to the plurality of tubes within the cooling cover 12 so as to allow the person 14 to rest comfortably even though the ambient temperatures within the bedroom are very high. As a result of the present invention, it is not necessary to fully air condition the bedroom. The cooling air generator 22 will consume much less energy than is required to air condition the entire room to a sufficient degree to provide comfort to the person 14.

Figure 2:
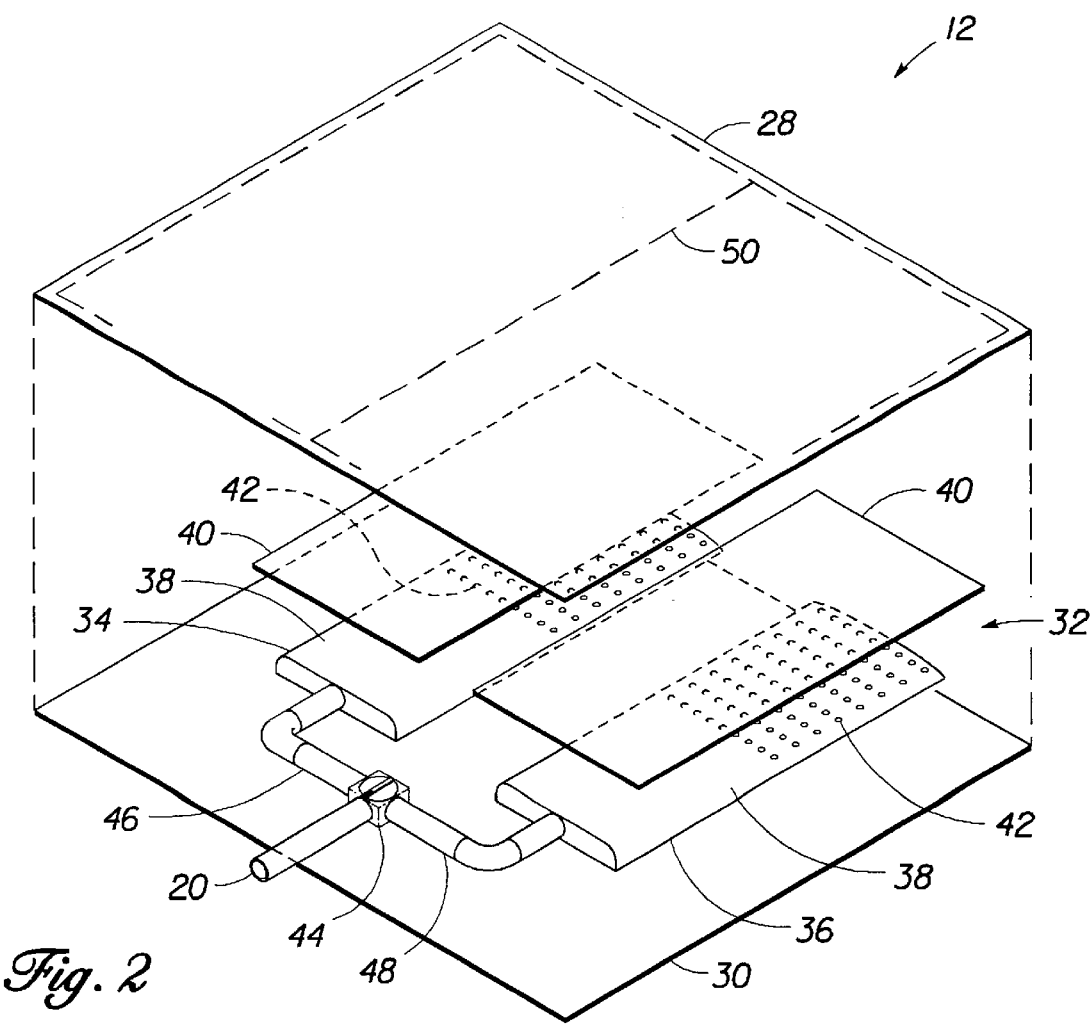
FIG. 2 is an exploded view showing the layered configuration of the preferred embodiment of the cooling cover apparatus of the present invention.

FIG. 2 shows an exploded view of the cooling cover 12 associated with the present invention. The cooling cover 12 includes a top sheet 28, a bottom sheet 30 and tubular members 32 positioned therebetween. The top sheet 28 can be secured to the bottom sheet 30 around its periphery. The plurality of tubular members 32 includes a first tubular member 34 and a second tubular member 36. Each of the tubular members 34 and 36 includes a foam insert 38 and a non-porous cover 40 affixed around its periphery to a surface of the foam insert 38. When the respective non-porous flexible covers 40 are secured to the foam inserts 38, the tubular member is formed. Each of the foam inserts 38 has an array of holes 42 formed therein. In the preferred embodiment of the present invention, this array of holes 42 is formed on the foam insert 38 in the half of the foam insert 38 away from the flexible hose 20. In this configuration, the holes 42 will be adjacent to the bottom sheet 30 so as to pass cooling air downwardly therethrough and outwardly of the bottom sheet 30 onto the person 14. The non-porous cover 40 will restrict air flow therethrough so that the cooling air is passed, with maximum cooling effect, downwardly toward the person 14. The positioning of the plurality of holes 42 in the distance half of the foam insert 38 causes the air to be directed toward the torso of the person 14 rather than to the feet of the person.

The flexible hose is connected to a diverter 44 which causes cooling air to pass, selectively, into either a first portion 46 or a second portion 48. The first portion 46 is connected to the first tubular member 44. The second portion 48 is connected to the second tubular member 36. The diverter 44 can be suitably manipulated by the person 14 so as to direct a desired cooling air flow to either one of the tubular members or to both of the cooling members. The diverter 44 is illustrated, in greater detail, in association with FIGS. 7 and 8. The top sheet 28 is joined to the bottom sheet 30 centrally along line 50. As such, the first tubular member 34 will be suitably isolated from the second tubular member 36 so as to maintain the desired position of the respective tubular members 34 and 36 in the area between the top sheet 28 and the bottom sheet 30.

Figure 3:
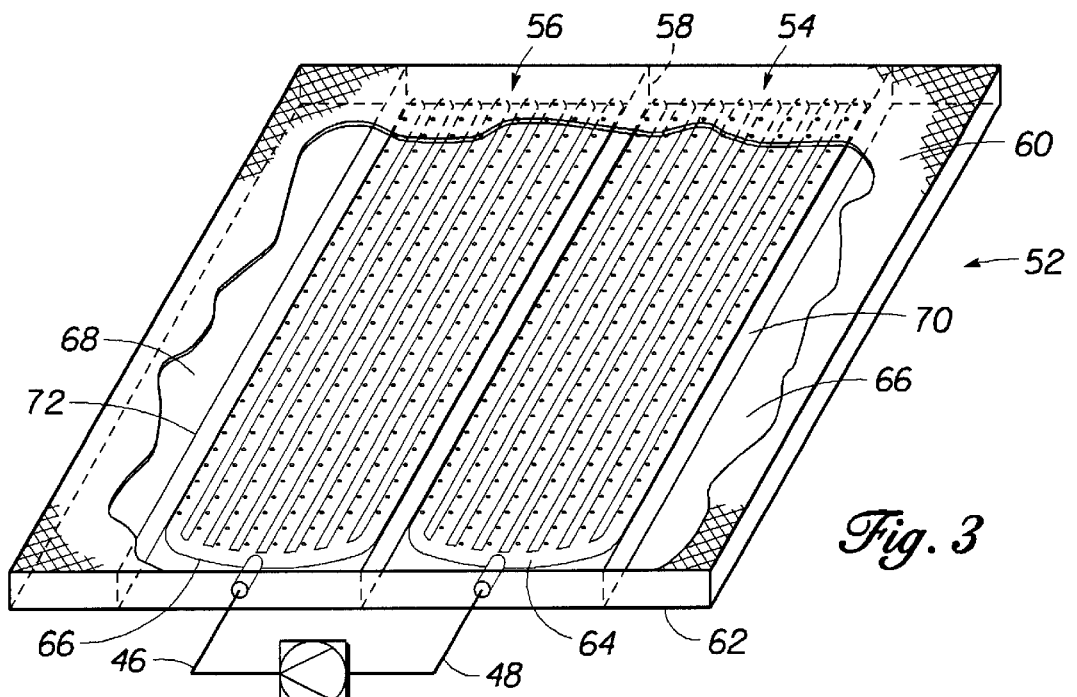
FIG. 3 is a perspective view in transparent illustration of the cooling cover apparatus in accordance with a first alternative embodiment of the present invention.

FIG. 3 shows an alternative embodiment 52 of the cooling cover apparatus of the present invention. The cooling cover apparatus 52 includes a first set of tubes 54 and a second set of tubes 56 positioned on opposite sides of a divider 58 formed between the top sheet 60 and the bottom sheet 62. The first set of tubes 54 includes a plurality of tubes which extend in generally parallel spaced relationship to each other. Each of the tubes in the first set of tubes 54 communicates with a first manifold 64. Similarly, each tube of the second set of tubes 56 is in spaced parallel relationship to an adjacent tube. Each of the tubes of the second set of tubes 56 communicates with a second manifold 66. The flexible hose 20 has a second portion 48 communicating with the first manifold 64 associated with the first set of tubes 54. Similarly, the first portion 46 of the flexible hose 20 is connected to the second manifold 66 so as to communicate with the tubes of the second set of tubes 56. The diverter 44 is in valved communication with the flexible hose, the first portion 46 and the second portion 48 so as to allow the user of the alternative embodiment 52 to selectively allow cooling air flow toward either the first set 54, the second set 56, or a combination thereof. The cooling unit 22 should be suitable so as to supply a sufficient supply of cooling air to the tubes of the first set 54 and the second set 56.

The tubes associated with the first set 54 or the second set 56 may be sealed at the end opposite the respective manifold 64 and 66. As such, all of the cooling air is directly forced outwardly of the holes formed along the length of the respective tubes. Since there is a pressure drop from the end adjacent to the respective manifolds 64 and 66 toward the opposite end of the tubes, the holes in each of the tubes should have a particular configuration so as to accommodate this pressure drop. As a result, the holes adjacent to the manifold 64 and 68 can have a smaller diameter that the holes approaching the opposite end. This allows a lesser flow of air to the feet of the person 14 and a greater flow of air toward the torso of the person. Alternatively, the holes can have a uniform size throughout but be spaced by a greater distance adjacent to the respective manifolds 64 and 66 than at the opposite end of the respective tubes.

In FIG. 3, it can be seen that the top sheet 60 and the bottom sheet 62 have a first overhang area 66 and a second overhang area 68. The first overhang area 66 extends outwardly of the first set of the tubes 54. The second overhang area 68 extends outwardly of the second set of the tubes 56. A suitable divider 70 can be positioned between the top sheet 60 and the bottom sheet 62 so as to maintain the first set of tubes 54 in their desired position within the cover. Similarly, another divider 72 can extend between the top sheet 60 and the bottom sheet 62 so as to maintain the second set of tubes 56 in their desired position. The overhang areas 66 and 68 are configured by joining the edges of the top sheet 60 to the bottom sheet 62. When the overhang areas 66 and 68 extend outwardly of the sides of the bed, they will form a seal therewith so as to prevent the unwanted flow of air easily outwardly therefrom.

Figure 4:
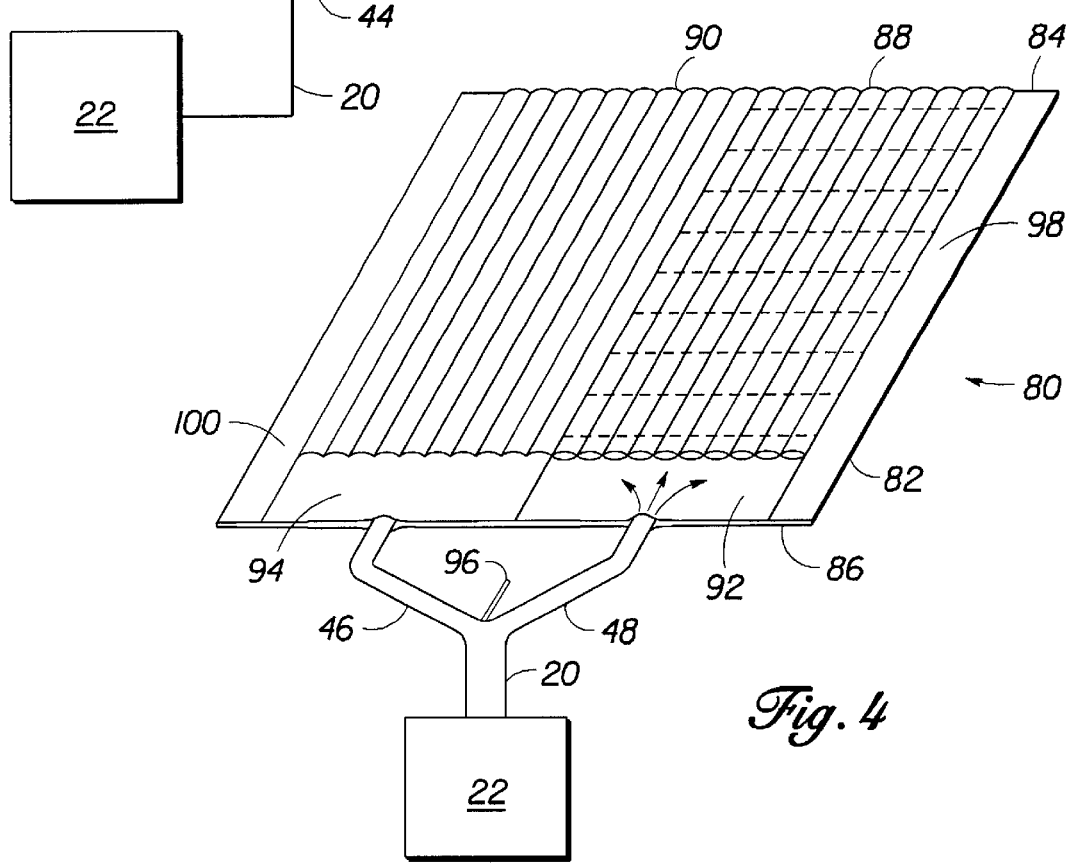
FIG. 4 is a perspective view of a second alternative embodiment of the cooling cover apparatus of the present invention.

FIG. 4 shows a second alternative embodiment 80 of the cooling cover apparatus of the present invention. The cooling cover apparatus 80 includes a cover 82 formed of a top sheet 84 and a bottom sheet 86. Unlike the previous embodiment, the plurality of tubes are cloth tubes formed by stitching parallel rolls of threads along the length of the cover 82. As a result, a first set of cloth tubes 88 and a second set of cloth tubes 90 are formed. The first set of cloth tubes 88 open, at one end, to a first manifold 92. The second set of cloth tubes 90 open, at one end, to a second manifold 94. The second portion 48 of the flexible hose 20 is connected to the first manifold 92. The first portion 46 of the flexible hose 20 is connected to the second manifold 94. As such, through the action of the cooling air generator 22, cooling air can pass into the respective manifolds 92 and 94 and henceforth through the cloth tubes formed in the first set of cloth tubes 88 and the second set of cloth tubes 90. Because of the porous nature of the bottom sheet 86, cooling air will pass to the person 14 residing therebelow. The top sheet could be formed of a non-porous material, if desired. A diverter 96 is positioned on the flexible hose 20 so as to selectively allow cooling air to pass into either the first portion 46 or the second portion 48 from the flexible hose 20. As such, by the proper manipulation of the diverter 96, the individual can chose the desired amount of cooling air flow to either the first set 88 or the second set 90 of the cloth tubes. Each of the cloth tubes associated with the first set 88 or the second set 90 are open at the end thereof opposite the manifolds 92 and 94, respectively. The cover 82 also has a first overhang area 98 and a second overhang area 100 formed in a similar manner to that shown in FIG. 3.

Figure 5:
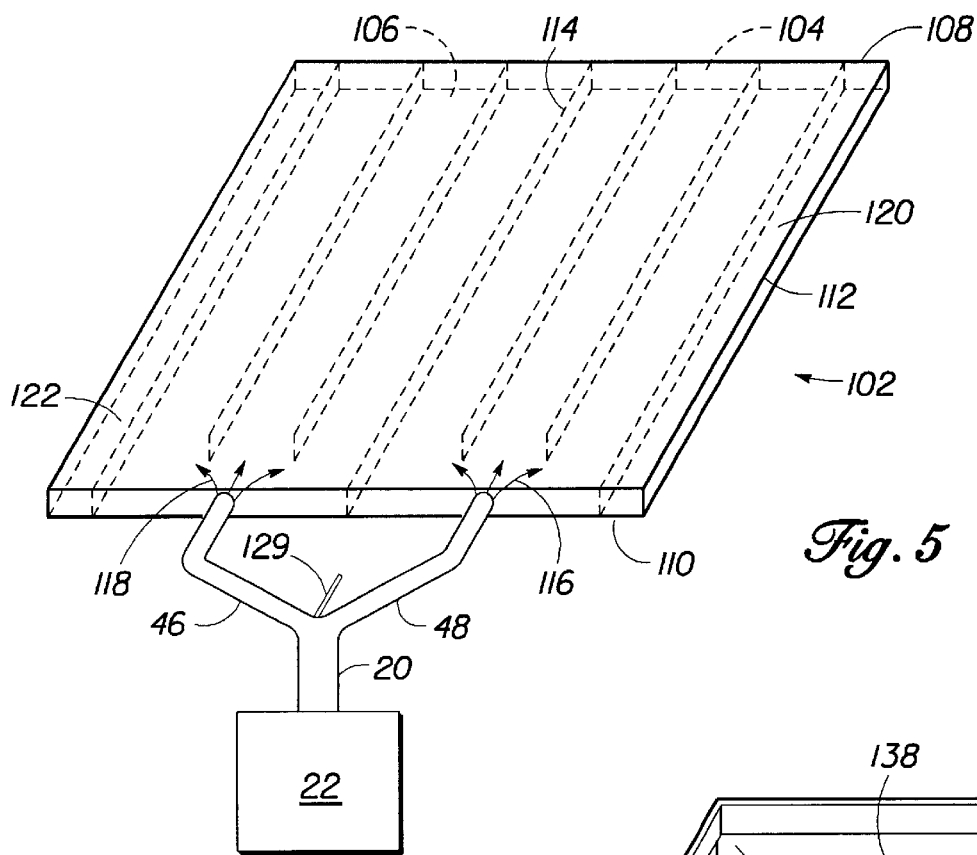
FIG. 5 is a perspective view of a third alternative embodiment of the cooling cover apparatus of the present invention.

FIG. 5 shows a third alternative embodiment of the present invention in which a first set of ducts 104 and a second set of ducts 106 are formed between the top sheet 108 and the bottom sheet 110 of cover 112. A central panel 114 separates the first set of ducts 104 from the second set of ducts 106.

Each of the ducts in the sets 104 and 106 are formed by a cloth strip extending generally transversely to the top sheet 108 and the bottom sheet 110. Each duct of the first set of ducts 104 has an end adjacent a first distribution area 116. Each duct of the second set of ducts 106 opens to a second distribution area 108. The second portion 48 of the flexible hose 20 is connected to and communicates with the first distribution area 116. The first portion 46 of the flexible hose 20 is connected to and communicates with the second air distribution area 118. As a result, the air can flow through each of the ducts. The porous nature of the bottom sheet 110 will allow cooling air to pass to the person 14 residing thereunder. Overhang areas 120 and 122 are formed on the sides of the cover 112 in the manner described herein previously. A diverter 124 functions similarly to the diverter 96 shown in FIG. 4.

Figure 6:
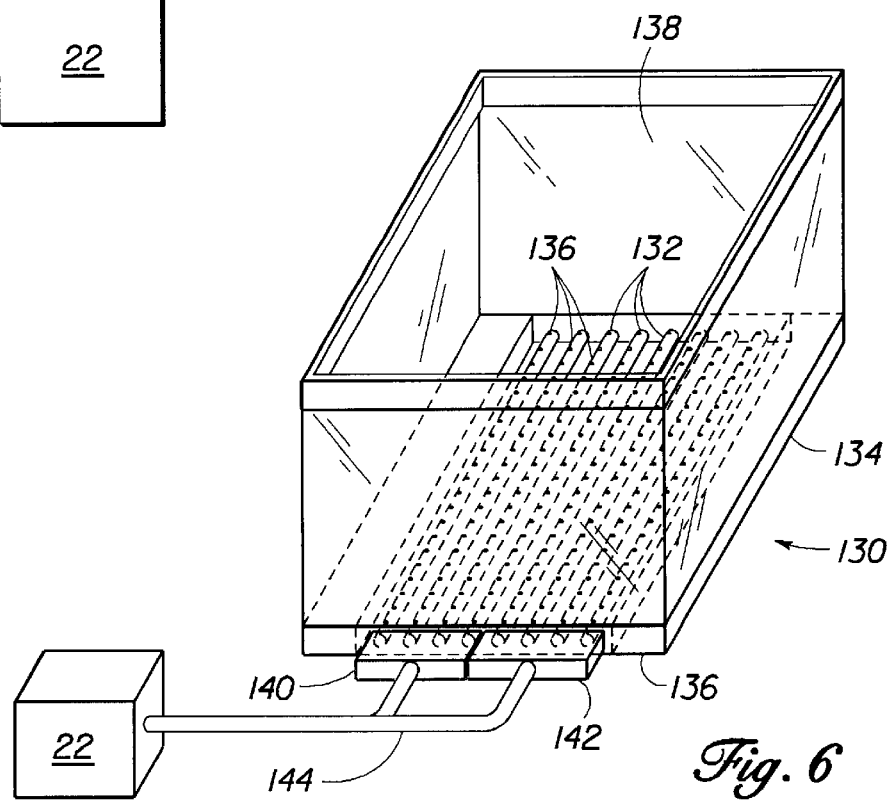
FIG. 6 is a partially exploded illustration of a fourth alternative embodiment of the cooling cover apparatus of the present invention.

FIG. 6 shows a fourth alternative embodiment 130 of the cooling cover apparatus of the present invention. The alternative embodiment 130 includes a plurality of channels 132 arranged in generally parallel relationship extending as channels through a foam pad 134. Each of the channels 132 has a plurality of holes 136 formed therein so as to allow cooling air to pass downwardly to the bottom sheet 136. The bottom sheet 136 can be a sheet affixed to the foam layer 134. A top sheet 138 is secured over the channels 132 in the foam pad 134. The top sheet 138 can be an impermeable sheet. As such, air introduced into the channels 132 is forced downwardly through the holes 136. A first manifold 140 and a second manifold 142 are connected to the flexible hose 144 extending from the cooling air generator 22. Manifolds 140 and 142 are associated with different sets of the channels 132.

Figure 7:
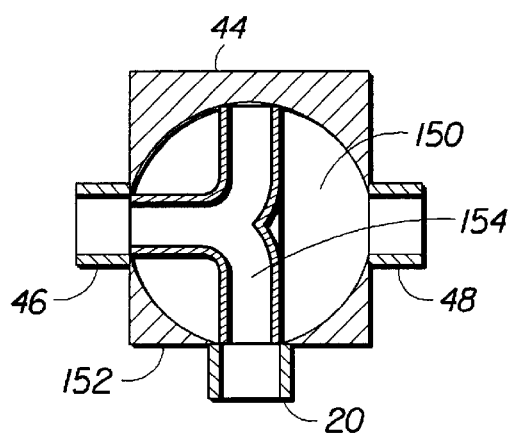
FIG. 7 is a diagrammatic illustration of the diverter used in the cooling cover apparatus of the present invention.

FIG. 7 shows a diagrammatic illustration of the diverter 44 associated with the present invention. The diverter 44 is an interior valve element 150 which is rotatably positioned within a housing 152. The valve element 150 has a T-shaped fluid passageway 154 therein. The diverter 44 is connected to the first portion 46 and to the second portion 48 and to the flexible hose 20. In this position shown in FIG. 6, cooling air from the flexible hose 20 passes through the fluid passageway 154 so as to be directed toward the first portion 46. A rotation of the valve element 150 counterclockwise will cause the fluid passageway 154 to be in communication with both the first portion 46 and the second portion 48 so that cooling air will pass from the flexible hose 20 through each of the first portion 46 and the second portion 48. When the valve element 150 is rotated still further counterclockwise, cooling air will pass from the flexible hose 20, through the fluid passageway 104 and only into the second portion 48. A further rotation of the valve element will cause cooling air to be blocked from going into either of the first portion 46 or the second portion 48.

Figure 8:
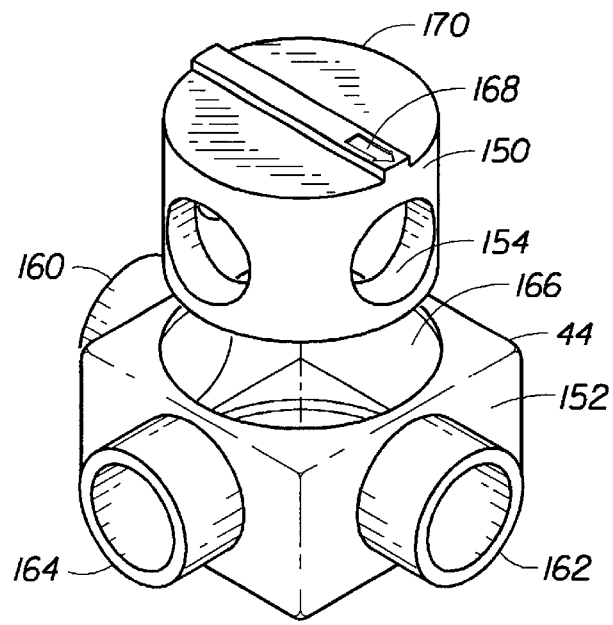
FIG. 8 is an exploded view of the diverter as used in the cooling cover apparatus of the present invention.

FIG. 8 shows a mechanical construction of the diverter 44. As can be seen, the housing 152 has annular connectors 160, 162, and 164. Annular connector 160 will be connected to the first portion 46. Annular connector 162 will be connector to the second portion 48. Annular connector 164 will be connected to the flexible hose 20. The valve element 150 is received within the interior 166 of the housing 152. Fluid passageway 154 is formed in the interior of the valve element 150. An indicator marking 168 is formed on the top surface 170 of the valve element 150 so as to allow the user to positively see the direction of cooling air flow.

In the present invention, the cooling air generator 22 can have a wide variety of configurations. For example, the cooling air generator can be an evaporative cooler, a thermoelectric cooler, or a vapor-compression cycle cooler. FIG. 7 shows a rolling piston rotary compressor 200 in accordance with the preferred embodiment of the present invention. It is believed that this rolling piston rotary compressor is the most suitable type of compressor for use in the present invention. This type of compressor is appropriate for small applications and is currently used in household refrigerators and in small air-conditioning units. The compact design and low noise level output make the rolling piston compressor an attractive choice for the present invention.

In the rolling piston rotary compressor, the compressor shaft 202 has an eccentric lobe on its end that effectively rolls the cylindrical piston 204 around the inside surface of the housing 206. A spring-loaded vane 208 separates the inlet port 210 from the outlet port 212. As the piston 204 rolls, the vacuum that it created will draw refrigerant into the housing 206. This rolling motion compresses the refrigerant ahead of the piston 204 thereby forcing it out of the discharge port 212. The discharge port 212 is equipped with a reed-type valve so as to prevent back flow.

The foregoing disclosure and description of the invention is illustrative and explanatory thereof. Various changes in the details of the illustrated construction may be made within the scope of the appended claims without departing from the true spirit of the invention. The present invention should only be limited by the following claims and their legal equivalents.

I claim:

1. A cooling cover apparatus comprising:
   a top sheet;
   a bottom sheet secured to said top sheet;
   a plurality of tubular members positioned between said top sheet and said bottom sheet, each of said plurality of tubular members having openings formed therein;
   a flexible hose interconnected to said plurality of tubular members with a diverter connected to said flexible hose so as to cause cooling air to selectively enter at least one of said plurality of tubular members; and
   a cooling air generator connected said flexible hose so as to pass cooling air through said flexible hose and into said plurality of tubular members.

2. The apparatus of claim 1, each of said plurality of tubular members comprising:
   a foam insert having a plurality of holes formed therein; and
   a non-porous cover affixed to said foam insert, said flexible hose connected to an end of said foam insert and said non-porous cover.

3. The apparatus of claim 2, said plurality of holes being formed only in a half of said foam insert opposite said flexible hose.

4. The apparatus of claim 2, said plurality of tubular members comprising two tubular members in spaced parallel relationship, said top sheet and said bottom sheet being affixed to each other between said two tubular members.

5. The apparatus of claim 4, further comprising:
   a diverter means connected to said flexible hose, said diverter means for causing cooling air to pass selectively into at least one of said two tubular members.

6. The apparatus of claim 1, said plurality of tubular members comprising:
   a first set of tubes positioned between said top and bottom sheets, each of the tubes of said first set being in spaced parallel relationship, said flexible hose having a first portion connected to a first manifold communicating with said first set of tubes;
   a second set of tubes positioned between said top sheet and said bottom sheet, each of the tubes of said first set being in spaced parallel relationship, said flexible hose having a second portion connected to a second manifold communicating with said second set of tubes; and
   said first and second sets having a plurality of holes formed therealong said plurality of holes being of increasing diameter away from the respective manifolds.

7. The apparatus of claim 6, said plurality of holes being progressively spaced closer together away from the respective manifolds.

8. The apparatus of claim 6, further comprising:
   a diverter means connected to said flexible hose and to said first and second portions, said diverter means for selectively passing cooling air into at least one of said first and second sets.

9. The apparatus of claim 1, said plurality of tubular members comprising:
   a first set of ducts positioned between said top and bottom sheets, each duct of said first set of ducts having an end opening to a first distribution area, said flexible hose having a first portion communicating with said first distribution area;
   a second set of ducts positioned between said top and bottom sheets, said ducts of said second set of ducts opening to a second distribution area, said flexible hose having a second portion communicating with said second distribution area; and
   a diverter means connected to said flexible hose and to said first and second portions, said diverter means for selectively passing cooling air into air at least one of said first and second sets of ducts.

\* \* \* \* \*